(12) United States Patent
Lewis

(10) Patent No.: US 7,442,042 B1
(45) Date of Patent: Oct. 28, 2008

(54) MAGNETIC CLIP CORD

(76) Inventor: Justin A. Lewis, 1902 Huntington La., Apt. #4, North Hollywood, CA (US) 90046

( * ) Notice: Subject to any disclaimer, the term of this patent is extended or adjusted under 35 U.S.C. 154(b) by 0 days.

(21) Appl. No.: 11/825,736

(22) Filed: Jul. 9, 2007

(51) Int. Cl.
H01R 13/60 (2006.01)
(52) U.S. Cl. ......................................... 439/39
(58) Field of Classification Search ............... 439/38, 439/39
See application file for complete search history.

(56) References Cited

U.S. PATENT DOCUMENTS

| | | | | |
|---|---|---|---|---|
| 3,786,391 | A | * | 1/1974 | Mathauser .................. 439/39 |
| 3,808,577 | A | * | 4/1974 | Mathauser .................. 439/39 |
| 3,868,160 | A | * | 2/1975 | Kersman .................... 439/39 |
| 4,451,113 | A | * | 5/1984 | Zuniga ....................... 439/40 |
| 4,917,612 | A | * | 4/1990 | Priest ......................... 439/39 |
| 6,183,264 | B1 | * | 2/2001 | Harsanyi .................... 439/38 |
| 6,213,736 | B1 | | 4/2001 | Weisser |
| D470,284 | S | | 2/2003 | Vega |
| 6,527,570 | B1 | | 3/2003 | Hartman et al. |
| 2002/0016088 | A1 | | 2/2002 | Wendelson et al. |
| 2002/0155754 | A1 | | 10/2002 | De'Longhi |
| 2005/0080407 | A1 | | 4/2005 | Ehr et al. |
| 2005/0082915 | A1 | | 4/2005 | Steinberg |

* cited by examiner

*Primary Examiner*—Briggitte R Hammond

(57) ABSTRACT

The invention is a magnetic clip cord for a tattoo machine that comprises a pair of magnet bars, in which one magnet bar is mounted to an electrical cord and the other magnet bar is mounted on the frame of a tattoo machine. The invention consists of an electrical cord, a spring, a set screw, two steel bars, two brass connectors, two non-conductive collars, two magnet bars, and a tattoo machine. The invention is used by aligning the two magnets bar, and allowing the magnetic force to connect the two pieces, upon which a positive current will pass along to a tattoo machine when in use. The steel bars carry the negative current and shall connect upon alignment of the magnet bars. The primary feature of the present invention is to prevent tattoo artisan errors attributed to outside forces acting on the power cord that attaches to the tattoo machine being used, by providing a magnetic clip cord design.

2 Claims, 3 Drawing Sheets

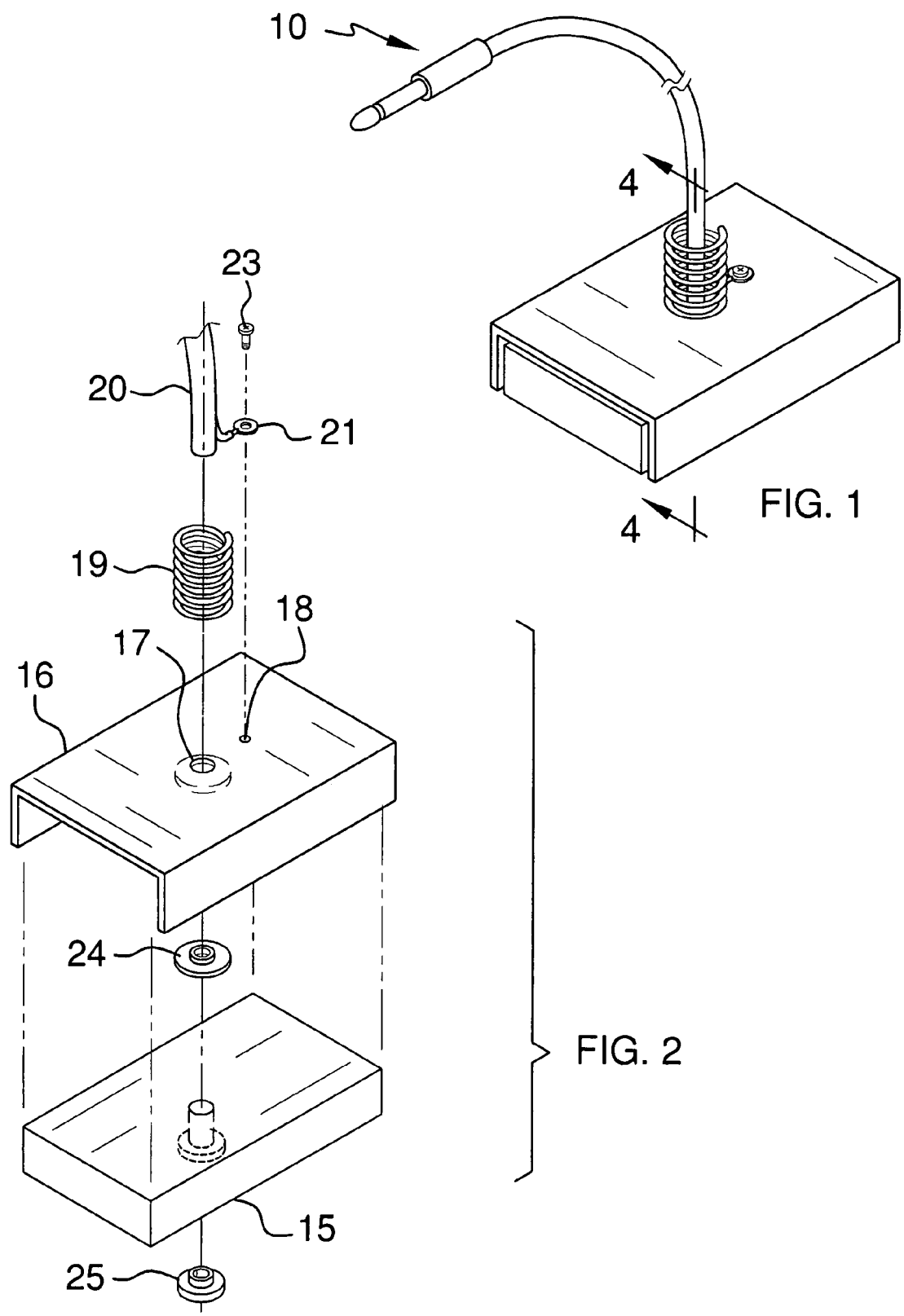

MAGNETIC CLIP CORD

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

This invention relates to the field of tattoo machines, more specifically, the cord used to supply electricity to a tattoo machine.

B. Discussion of the Prior Art

The Steinberg Patent Application Publication (U.S. Pub. No. 2005/0082915) discloses a breakaway power cord having two connectors that are magnetically attracted with a first connector running to an appliance and a second connector running to a power source. However, this invention does not utilize a steel plate magnetically attracted to a magnet mounted on a tattoo machine.

The De'Longhi Patent Application Publication (U.S. Pub. No. 2002/0155754) discloses an electrical cord with a connection plug that magnetically connects to a magnetized member associated with a kitchen appliance. However, this applies to the field of preventing condensation in and around the power supply of kitchen appliances as opposed to a magnetically stabilized connection between a tattoo machine's power cord and the tattoo machine.

The Weisser patent (U.S. Pat. No. 6,213,736) discloses a magnetic power coupling and thrust balancing means for use in the prevention of failure in submerged electric pumps associated with cracks between electric windings of the stator and the surrounding corrosive liquid. However, this use does not coincide with the need to create a secure power connection while operating a tattoo machine, and correspondingly tattoo machines do not use electric motors submerged in corrosive surroundings that cause failure to the electric stator.

The Mendelson et al. Patent Application Publication (U.S. Pub. No. 2002/0016088) discloses a detachable power supply apparatus that for use with electrical appliances including removable temperature control devices in which a mounting panel on the temperature control device to which an electrical connector on a power supply cord is magnetically and electrically coupled. The tattoo machine in the present invention utilizes a power cord that has a steel plate permanently affixed to itself in which the steel plate is magnetically and electrically coupled to a magnet bar that is mounted on the frame of the tattoo machine. Furthermore, the present invention does not utilize a temperature control device used in conjunction with the magnetically and electrically coupled connection.

The Ehr et al. Patent Application Publication (U.S. Pub. No. 2005/0080407) discloses a return pad cable connector for use with a disposable return pad with a magnetic power coupling. However, this invention has a medical use involving a disposable pad that can involve a magnetic power coupling, whereas, the present invention relates to the need to provide a secure source of electricity while operating a tattoo machine.

The Hartman et al. patent (U.S. Pat. No. 6,527,570) discloses a quick-release plug assembly having a plug body and a socket body for receiving the plug body, wherein either the plug body or the socket body includes a magnet and the corresponding body has an attractive member. However, this invention does not utilize a steel plate integrated into the design of the electrical cord in which the steel plate is magnetically attracted to a magnet bar that is mounted to the frame of a tattoo machine.

The Vega patent (U.S. Pat. No. Des. 470,284) illustrates a design for a magnetically coupled double-sided window washer, which does not involve or illustrate a supply of electricity or a tattoo machine.

BRIEF SUMMARY OF THE INVENTION

The invention is a magnetic clip cord for a tattoo machine that comprises a pair of magnet bars, in which one magnet bar is mounted to an electrical cord and the other magnet bar is mounted on the frame of a tattoo machine. The invention consists of an electrical cord, a spring, a set screw, two steel bars, two brass connectors, two non-conductive collars, two magnet bars, and a tattoo machine. The invention is used by aligning the two magnets bar, and allowing the magnetic force to connect the two pieces, upon which a positive current will pass along to a tattoo machine when in use. The steel bars carry the negative current and shall connect upon alignment of the magnet bars. The primary feature of the present invention is to prevent tattoo artisan errors attributed to outside forces acting on the power cord that attaches to the tattoo machine being used, by providing a magnetic clip cord design.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention:

In the drawings:

FIG. 1 illustrates an isometric view of the steel bar assembly of the invention;

FIG. 2 illustrates an exploded view of the steel bar assembly of the invention;

DETAILED DESCRIPTION OF THE EMBODIMENT

Figure 3:
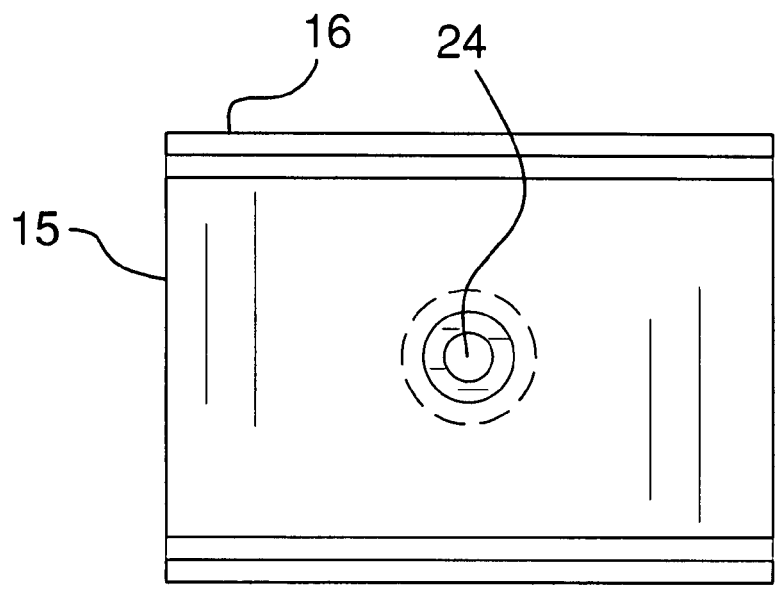
FIG. 3 illustrates a bottom-side view of the steel bar assembly of the invention.
Figure 4:
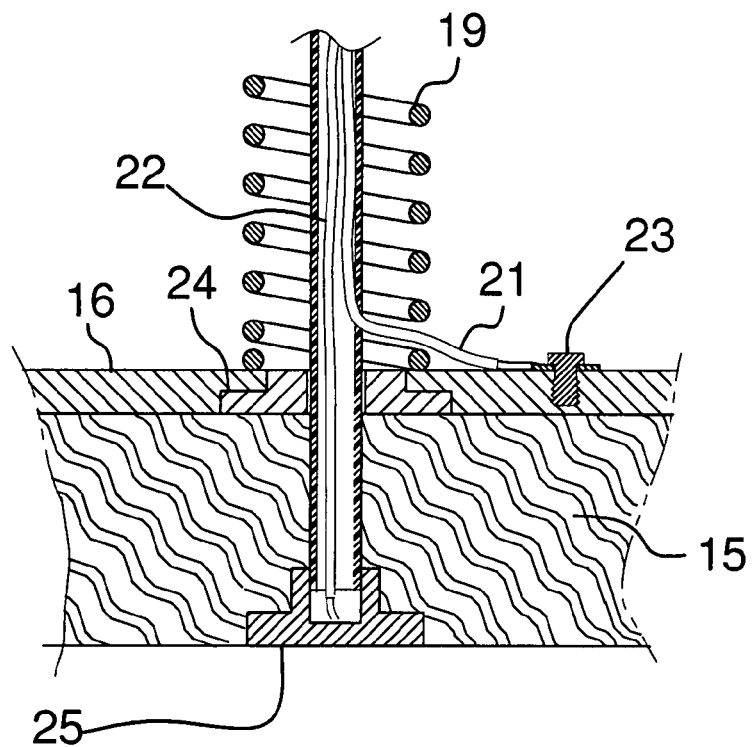
FIG. 4 illustrates a cross-sectional view of the steel bar assembly of the invention along line 4-4.

Detailed reference will now be made to the preferred embodiment of the present invention, examples of which are illustrated in FIGS. 1-5. A magnetic clip cord 10 (hereinafter invention) involves a magnet bar 15, a steel bar 16, a spring 19, and a power cord 20. The steel bar 16 has a big hole 17, and a little hole 18 located on the top surface of the steel bar 16. Co-axially Located above the big hole 17, is the spring 19. The power cord 20 contains a negative wire 21, and a positive wire 22. An end of the negative wire 21 runs out the bottom of the power cord 20, through the spring 19, and connects to the top surface of the steel bar 16 by a screw 23, which screws into the little hole 18.

A non-conducting collar 24 is fitted into the bottom side of the big hole 17 of the steel bar 16. Protruding from the end of the power cord 20 is the positive wire 22, which connects to a brass connector 25. The non-conducting collar 24 is seated between the surface of the steel bar 16 and the brass connector 25. The non-conducting collar 24 is made of a non-conductive material such as plastic.

Figure 5:
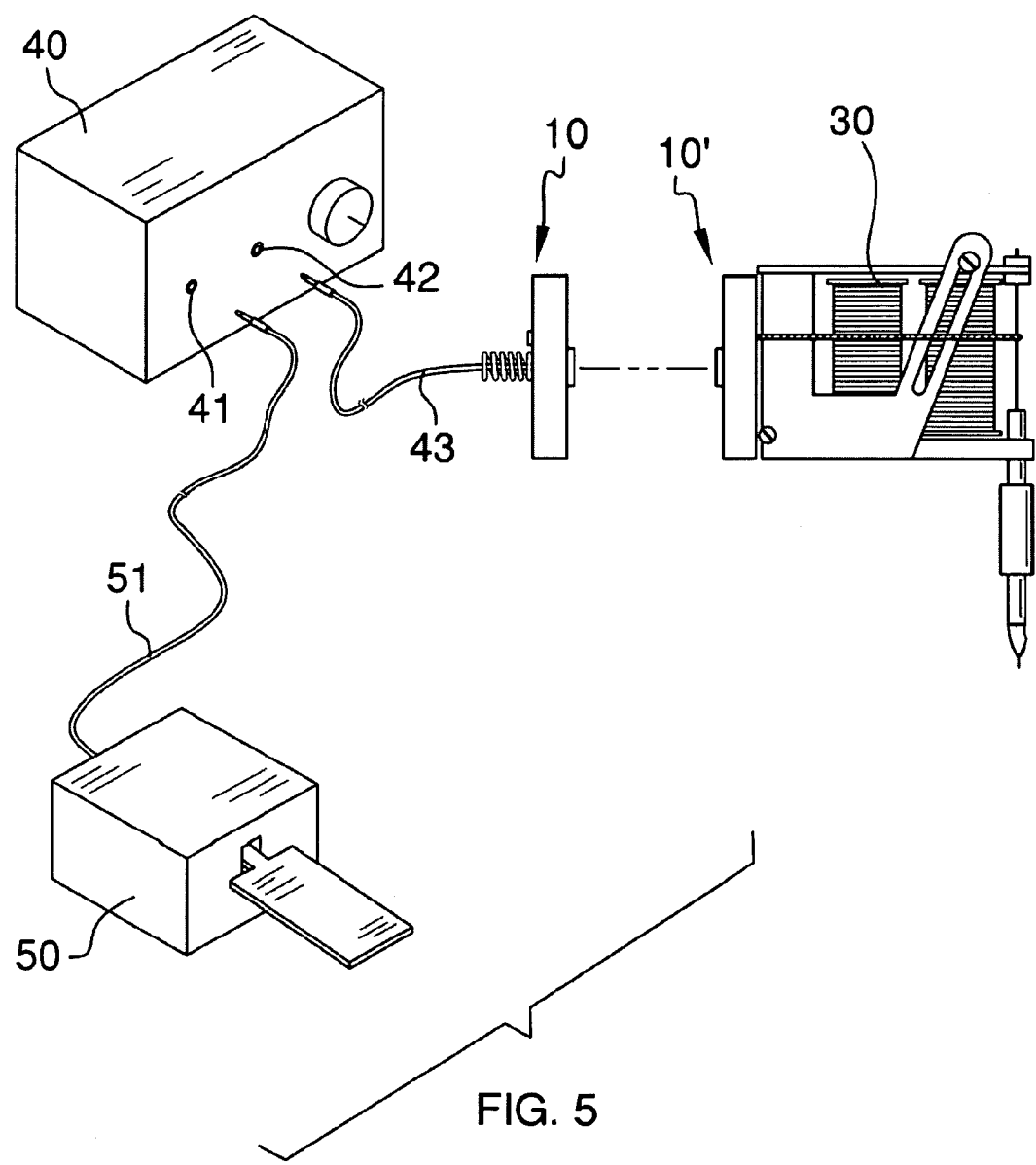
FIG. 5 diagrams all of the components, including the invention, in a typical tattoo machine layout.

Mounted to a side of a tattoo machine 30, is an invention 10', which is depicted in FIG. 5. The invention 10' involves a magnet bar 15, a steel bar 16, the tattoo machine's power cord (not shown), a non-conducting collar 24, and a brass collar 25.

The tattoo machine's power cord (not shown) connects to the invention 10' in the same way as the power cord 20 connects to the invention 10. The tattoo machine's power cord (not shown) will consist of a negative wire and a positive wire.

The negative wire of the tattoo machine's power cord connects to the steel bar 16 of the invention 10' by a screw 23. The positive wire of the tattoo machine's power cord (not shown) shall be directed to the brass collar 25 of the invention 10'.

Referring to FIG. 5, the invention 10 and the invention 10' are aligned such that the magnet bar 15, brass collar 25, and the steel bars 16 are aligned with each other, respectively. The magnetic force between the two magnet bars 15 will pull both the invention 10 and the invention 10' together, such that the two brass connectors 15 will touch one another, and enable the positive electrical current to pass from the invention 10 to the invention 10'. Additionally, the sides of the two steel bars 16 will also touch one another, and enable the negative electrical current to pass from the invention 10 to the invention 10'.

Meanwhile, the power cord 20 plugs into a power supply box 40 at a power out plug 42. A foot pedal 50 connects to the power supply box 40 by a foot pedal cord 51, which plugs into the power supply box 40 at a foot pedal plug 41.

Once all of the components of the invention 10 are connected, the would be tattooer will engage his or her foot on the foot pedal 50 so as to turn on the power supply to the tattooing machine 30.

The inventor claims:

1. An improved magnetic clip cord for a tattoo machine comprising:
   (a) a magnet bar;
   (b) a metal bar;
      wherein along a top surface of the metal bar, at predetermined locations are big hole and a small hole;
      wherein the metal bar has a shape that is slightly larger than a cross-section of the magnet, and is U-shaped, so that when placed over the magnet bar, the metal bar does not touch any surface of the magnet bar;
   (c) a power cord consisting of a coaxially insulated positive wire and a coaxially insulated negative wire run throughout the power cord;
   (d) a spring;
      wherein the spring provides positive upward direction for a bottom of the power cord;
   (e) a brass connector;
      wherein a end of the positive wire protrudes from the bottom of the power cord and is permanently affixed to the brass connector;
   (f) a screw;
      wherein the end of the negative wire protrudes from the bottom of the power cord, through an opening in the spring, and is permanently affixed to the top surface of the metal bar by the screw at the predetermined location where the small hole exists; and
   (g) a non-conducting collar;
      wherein the non-conducting collar is fitted between the bottom surface of the big hole of the metal bar and the brass connector; and
   wherein attached to a tattoo machine is a second metal bar and a second magnet bar with a second nonconducting collar and second brass connector;
   wherein a power cord of the tattoo machine consists of a positive wire and a negative wire;
   wherein the positive wire is attached to the second brass connector;
   wherein the negative wire is attached to the second metal bar;
   wherein the two magnet bars will attract each other via the magnetic force which will in turn cause both brass connectors to touch, and simultaneously cause both metal bars to touch, thereby enabling electrical current to pass to the tattoo machine; and
   wherein the flow of electrical current to the tattoo machine is stopped by the separation of the two magnet bars.

2. The non-conducting collar as described in claim 1 wherein the non-conducting collar is made from a plastic.

* * * * *